United States Patent [19]

Houghton et al.

[11] Patent Number: 4,977,258
[45] Date of Patent: Dec. 11, 1990

[54] BENZOXAZEPINONE PROCESS

[75] Inventors: Peter G. Houghton, Bassingbourn, Nr. Royston; Stanley H. B. Wright, Sawbridgeworth, both of England

[73] Assignee: Merck, Sharp & Dohme Ltd., Hertfordshire, England

[21] Appl. No.: 414,222

[22] Filed: Sep. 29, 1989

[30] Foreign Application Priority Data

Oct. 6, 1988 [GB] United Kingdom ............... 8823475

[51] Int. Cl.$^5$ ......................................... C07D 498/04
[52] U.S. Cl. .................................................. 540/548
[58] Field of Search ......................................... 340/548

[56] References Cited

U.S. PATENT DOCUMENTS 4,622,320 11/1986 Ferrosan ............................. 540/548
4,622,321 11/1986 Ferrosan ............................. 540/548
4,880,799 11/1989 Watger ............................... 514/211

FOREIGN PATENT DOCUMENTS 0109921 11/1983 European Pat. Off. ............ 540/548
0150040 1/1985 European Pat. Off. ............ 540/548

Primary Examiner—Robert Gerstl
Attorney, Agent, or Firm—Manfred Polk; Joseph F. DiPrima

[57] ABSTRACT

Compounds of formula III:

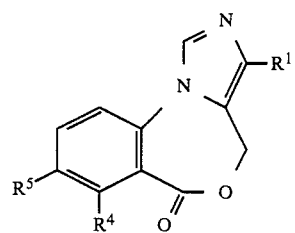

wherein $R^1$ is a 5- or 6-membered aromatic heterocyclic group; and $R^4$ and $R^5$ each idependently signify hydrogen, halogen, trifluoromethyl, cyano, nitro, amino or lower alkyl; are useful intermediates in a novel process for the preparation of a class of pharmacologically active compounds of formula I:

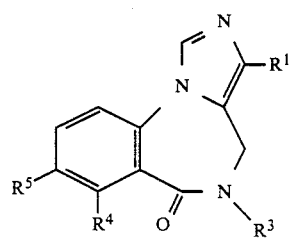

wherein $R^1$, $R^4$ and $R^5$ are as defined above; and $R^3$ represents hydrogen or lower alkyl.

8 Claims, No Drawings

BENZOXAZEPINONE PROCESS

This invention relates to a class of chemical compounds useful as intermediates and in particular to a class of imidazobenzoxazepinone derivatives. The intermediates are useful in a novel process for the preparation of a class of pharmacologically active imidazobenzodiazepine compounds.

Certain imidazobenzodiazepines having anxiolytic, anticonvulsant, muscle-relaxant and sedative-hypnotic properties are disclosed in European patent specification No. 150,040. That specification discloses, inter alia, compounds having the formula I:

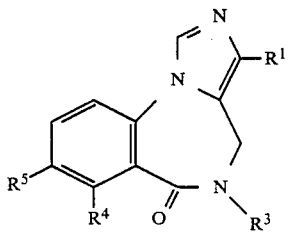

in which $R^1$ is a 5- or 6-membered aromatic heterocyclic group; $R^3$ represents hydrogen or lower alkyl; and $R^4$ and $R^5$ each independently signify hydrogen, halogen, trifluoromethyl, cyano, nitro, amino or lower alkyl. European patent specification No. 109,921 describes a group of compounds within the formula I above in which $R^1$ represents an oxadiazolyl group, having a $C_{1-3}$ alkyl substituent. Furthermore, U.S. Pat. Nos. 4,622,320 and 4,622,321 disclose further compounds within general formula I in which $R^1$ represents a cyclopropyl-substituted oxadiazolyl group.

The processes described in the above patents for the preparation of compounds of type I above start from an imidazobenzodiazepine nucleus of formula II:

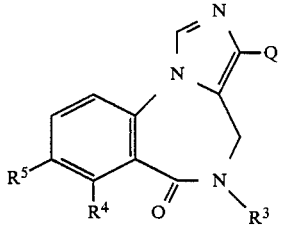

in which Q represents a group which may be converted into a heterocyclic group $R^1$. Thus the heterocyclic ring is incorporated in the final synthetic step.

The present invention is based on a novel imidazobenzoxazepine ring system which includes a heterocyclic substituent and which may then be converted into a heterocyclyl-substituted imidazobenzodiazepine.

Accordingly the present invention provides a compound of formula III:

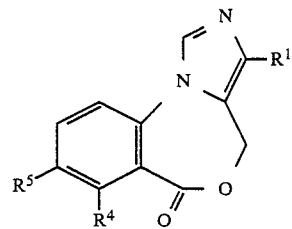

wherein $R^1$, $R^4$ and $R^5$ are as defined above with respect to formula I.

Preferred groups $R^4$ and $R^5$ are hydrogen, halogen or trifluoromethyl, in particular hydrogen, fluoro, chloro or bromo.

The group $R^1$ represents an aromatic heterocyclic ring containing 5 or 6 atoms, up to three of which may be selected from oxygen, nitrogen and sulphur. Suitable groups $R^1$ include oxazolyl, thiazolyl, oxadiazolyl, thiadiazolyl, pyrazinyl and pyrimidinyl. Particularly suitable groups $R^1$ are 1,2,4-oxadiazol-3-yl, 1,2,4-oxadiazol-5-yl, 1,3,4-oxadiazol-2-yl, 1,2,4-thiadiazol-3-yl, 1,3,4-thiadiazol-2-yl and 1,2,5-thiadiazol-b 3-yl.

The aromatic heterocyclic group $R^1$ may be unsubstituted or substituted on a carbon atom. Suitable substituents include $C_{1-5}$ alkyl, $C_{3-6}$ cycloalkyl, trifluoromethyl, phenyl, amino, $C_{1-6}$ alkylamino, $C_{1-6}$ alkoxy($C_{1-6}$)alkyl or hydroxy. Preferred substituents for the group $R^1$ are $C_{1-4}$ alkyl, such as methyl, ethyl, n-propyl, isopropyl and t-butyl; and $C_{3-6}$ cycloalkyl, especially cyclopropyl.

One sub-group of compounds of this invention is represented by formula IV:

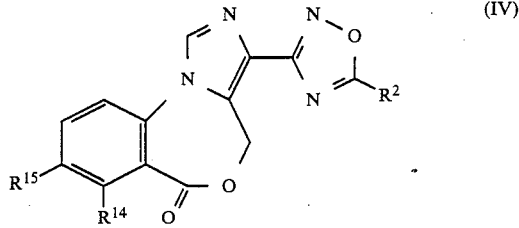

wherein $R^{14}$ and $R^{15}$ independently represent hydrogen, fluoro, chloro or bromo; and $R^2$ represents hydrogen, $C_{1-4}$ alkyl or $C_{3-6}$ cycloalkyl. Preferably $R^2$ represents hydrogen, methyl, n-propyl, isopropyl, t-butyl or cyclopropyl.

The benzoxazepinone compounds of this invention are valuable intermediates for the preparation of benzodiazepines of formula I above. Accordingly the present invention also provides a process for the preparation of a compound of formula I above, which process comprises the following steps:

(a) aminolysis of a benzoxazepinone of formula III to form an amide of formula V:

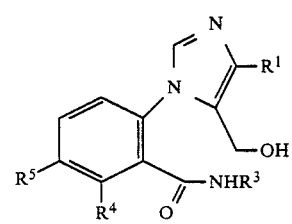

wherein R¹, R⁴ and R⁵ are as defined above with reference to formula I; and R³ represents hydrogen or C₁₋₆ alkyl;

(b) halogenation of compound V to form a compound of formula VI:

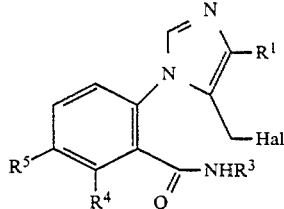

(VI)

wherein R¹, R³, R⁴ and R⁵ are as defined above; and Hal represents chlorine or bromine; and (c) cyclisation of compound VI to form a compound of formula I.

The compounds V and VI are also novel and represent further aspects of this invention.

Furthermore the steps (a), (b) and (c) above each represent novel processes individually and each forms a further aspect of this invention.

Process (a) of the synthetic sequence comprises the aminolysis of a benzoxazepinone of formula III. Suitable reagents for this process are ammonia or C₁₋₆ alkylamine, such as methylamine, propylamine or butylamine. The amine is chosen to provide the nitrogen substituent group R³ in the final product of formula I. The process may be carried out in a polar solvent such as ethanol, water, dimethylformamide, or mixtures thereof. Ambient temperatures are suitable for this process, for example from 15° C. to 30° C., especially 20° C. to 25° C.

Process (b) of the synthetic sequence comprises the halogenation of the compound V to give a haloamide of formula VI. Any suitable halogenating agent may be employed in this process. Preferably, the halogen group Hal in formula VI is chlorine. Suitable chlorinating agents include thionyl chloride, methanesulphonyl chloride and phosphorus oxychloride. The reaction may be carried out in an inert anhydrous solvent such as tetrahydrofuran or dimethylformamide, suitably at a temperature of from 0° C. to 25° C.

Process (c) of the synthetic sequence comprises the cyclisation of compound VI to form a benzodiazepine of formula I. Suitably this cyclisation is effected by means of a strong organic base, such as sodium hydride or potassium t-butoxide. The temperature at which the process is carried out is dependent on the base used. For example, potassium t-butoxide is employed at low temperatures, such as −40° C. to −20° C. A suitable solvent is tetrahydrofuran. Sodium hydride may be used at ambient or elevated temperatures such as 20° C. to 100° C. A suitable solvent is again tetrahydrofuran.

The final product of formula I may be isolated by conventional methods such as crystallisation, solvent extraction or chromatography.

The benzoxazepinone compounds of formula III of this invention may be prepared from a compound of formula VII:

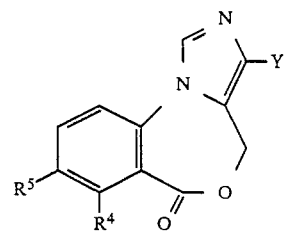

(VII)

wherein R⁴ and R⁵ are as defined above; and Y represents a group which may be converted into a 5- or 6-membered aromatic heterocyclic ring.

The process for converting the group Y into a 5- or 6-membered aromatic heterocyclic ring may be carried out by conventional methods. Examples of suitable groups Y include —CN, —CONH₂, —C(NH₂)=NOH and —CORᵃ; where Rᵃ represents a leaving group, e.g. C₁₋₆ alkoxy.

In particular, compounds of formula III in which the group R¹ represents oxadiazolyl may be prepared by:

(i) reacting a reactive derivative of a compound of formula VII above wherein Y represents —CO₂H, with a compound of formula:

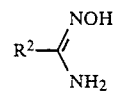

wherein R² is as defined with respect to formula IV above, to form a compound of formula III wherein R¹ is:

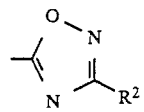

in which R² is as defined above; or (ii) reacting a compound of formula VII above where Y represents —CN, with hydroxylamine or a salt thereof, e.g. the hydrochloride, to form a compound of formula VII where Y represents:

and reacting that product with an anhydride of formula (R²CO)₂O, where R² is as defined with respect to formula IV above, to form a compound of formula III wherein R¹ is:

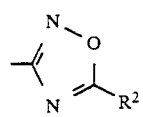

in which R² is as defined above.

Process (i) above may be carried out at a temperature of from 20° C. to 150° C. for a time of from 1 to 5 hours. Suitable solvents include tetrahydrofuran, dimethylformamide, toluene and xylene.

In process (ii), the reaction with hydroxylamine may be carried out in a polar solvent such as ethanol or isopropanol, suitably at reflux temperature, for a time of from 3 hours to 4 days. The subsequent reaction with the anhydride may be carried out with the anhydride reactant itself acting as solvent, suitably at a temperature of from 80° C. to 160° C., for a time of from 1 to 6 hours.

Other examples of the group Y which may be converted into a 5- or 6-membered aromatic heterocyclic ring are the same as the group Q in European patent specification No. 150,040.

The benzoxazepinone compounds of formula III may also be prepared by reacting a compound of formula VIII:

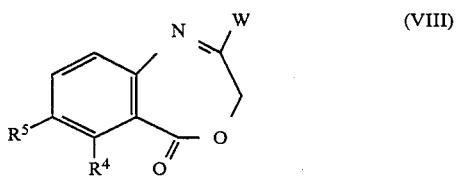

where $R^4$ and $R^5$ are as defined above, and W represents a leaving group; with an isocyanide of formula $CN-CH_2-R^1$ in the presence of a base.

Suitable bases for this reaction include lithium diisopropylamide and potassium hexamethyl-disilazide. The leaving group W is preferably chlorine.

The compound of formula VII may also be prepared from the compound VIII above by reaction thereof with an isocyanide of formula $CN-CH_2-Y$ in the presence of a base, e.g. triethylamine.

The benzoxazepinone of formula VIII may be prepared by the following reaction sequence:

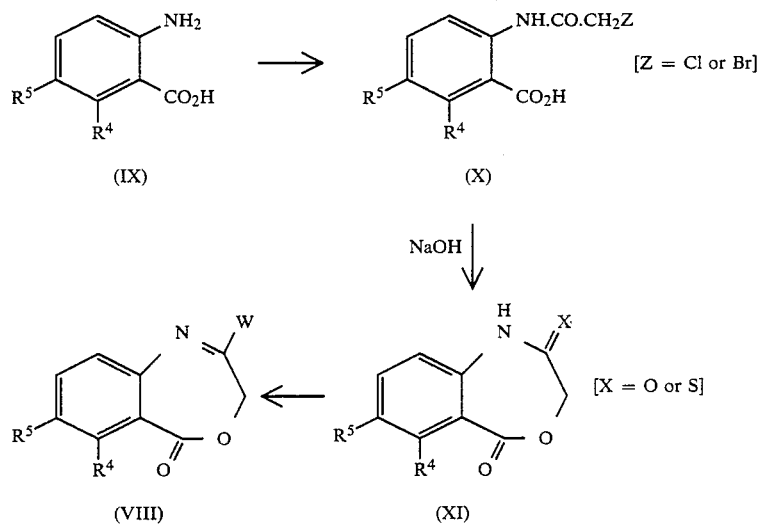

Treatment of the anthranilic acid IX with either chloroacetyl chloride or bromoacetyl bromide in dimethylformamide at room temperature provides the amide X. The amide X is then cyclised to give the benzoxazepine XI. This cyclisation may be carried out by heating the amide alone in refluxing dimethylformamide or by the use of a base, for example potassium fluoride in acetonitrile, potassium carbonate in methyl ethyl ketone, or, preferably, sodium hydroxide in isopropyl alcohol.

Treatment of the dione XI, X=O, with phosphoryl chloride and N,N-dimethylaniline in dichloromethane yields the imidoyl chloride VIII, W=Cl.

Alternatively, treatment of the thione XI, X=S, with sodium hydride followed by methyl iodide in tetrahydrofuran provides an imidothiolic ester VIII, W=SMe.

The following Examples illustrate the processes and compounds of this invention:

PREPARATION A

3-Isocyanomethyl-5-isopropyl-1,2,4-oxadiazole (a) Formamidoacetonitrile

Aminoacetonitrile hydrochloride (348 g) in boiling methyl formate (1.88 l) was treated with triethylamine (570 ml), added over 10 minutes, and the mixture heated under reflux for 22 hours. The mixture was cooled to 0° C. and the triethylamine hydrochloride removed by filtration and washed with ethyl acetate. The filtrate was washed with saturated potassium carbonate (300 ml), dried and evaporated. The residue was distilled (short-path) at 135° C./0.1 mm to give the product (211 g, 67%).

(b) Formamidoacetamidoxime

Sodium metal (20.7 g) was dissolved in dry methanol (259 ml) and the resulting solution added to a hot solution of hydroxylamine hydrochloride (62.1 g) in dry methanol (448 ml). The resulting mixture was stirred and heated under reflux for 10 minutes and then cooled to room temperature. The mixture was filtered to remove sodium chloride and the filtrate was then added to formamidoacetonitrile (37.8 g) at 5° C. The solution was then placed in the cold room for several days to yield the product as a highly crystalline white solid, 40 g, 76% yield obtained in two crops.

(c) 3-Formamidomethyl-5-isopropyl-1,2,4-oxadiazole

Sodium metal (2.3 g) was dissolved in absolute ethanol (500 ml) and then formamidoacetamidoxime (50 g) and dried 4A molecular sieves (50 g) added. The mixture was stirred at room temperature for 5 minutes and then ethyl isobutyrate (118 ml) added. The resulting mixture was heated under reflux under nitrogen atmosphere for 6 hours and then cooled to room temperature. The mixture was filtered through Hyflo to remove the sieves and then the solvent removed in vacuo at 40° C. The residue was dissolved in dichloromethane (500 ml) and treated with charcoal (5 g) and Na$_2$SO$_4$ (5 g). The mixture was filtered through Hyflo and the solvent removed in vacuo to yield the product as a dark oil, 46.3 g, 64%. Purity 85-90% (NMR).

(d) 3-Isocyanomethyl-5-isopropyl-1,2,4-oxadiazole

Formamidomethyloxadiazole (24.1 g) was dissolved in dichloromethane (156 ml) containing triethylamine (90 ml) at −20° C. Phosphoryl chloride (13.3 ml) was added dropwise over 10 minutes keeping the temperature below −5° C. for 1 hour. A solution of sodium carbonate (21.4 g) in water (120 ml) was added at <5° C. and the mixture stirred at room temperature for 1 hour. The mixture was filtered and the filtrate liquors separated. The aqueous layer was extracted with dichloromethane (2×50 ml). The organic layers were combined and washed with brine (100 ml), dried (Na$_2$SO$_4$) and evaporated to give a dark coloured oil. The oil was distilled (90° C., 0.4 mmHg) to give the product as a pale yellow oil, 13.2 g, 64% yield. Purity >99% (by NMR and LC).

EXAMPLE 1

4,1-Benzoxazepin-2,5-dione (XI; R$^4$=R$^5$=H, X=O)

A solution of sodium hydroxide (2 g, 50 mole) in water (12 ml) was added to a stirred slurry of 2-chloroacetamidobenzoic acid (10.3 g, 48 mmole) in isopropanol (22.5 ml) and water (87.5 ml). The mixture was stirred until a solution formed and then heated at 80° C. for 4 hours. The solution was cooled to 0° C. and the crystalline solid collected, washed with water and dried in vacuo at 50° C. to give the product (7.4 g, 87%), m.p. 200°-201° C.

EXAMPLE 2

6-Chloro-4,1-benzoxazepin-2,5-dione (XI; R$^4$=Cl, R$^5$=H, X=O)

Chloroacetyl chloride (51 ml, 0.64 mole) was added dropwise to a solution of 2-amino-6-chlorobenzoic acid (100 g, 0.58 mole) in dimethylformamide (150 ml) at <30° C. The solution was stirred for 1 hour at <30° C. and then treated with a solution of sodium hydroxide (52.2 g, 1.3 mole) in water (1.25 l). The mixture was stirred for 15 minutes, then heated to 90° C. to dissolve the solid and solution maintained at 90° C. for 2 hours. The solution was cooled to 0° C and the crystalline solid collected, washed with water and dried in vacuo at 50° C. to give the product (111.7 g, 91%), m.p. 193°-196° C.

EXAMPLE 3

4,1-Benzoxazepin-5-one-2-thione (XI; R$^4$=R$^5$=H, X=S)

4,1-Benzoxazepin-2,5-dione (4.5 g, 25 mmole) in dimethoxyethane (125 ml) was treated with Lawesson's reagent (12 g, 30 mmole) and the mixture was stirred at room temperature for 24 hours. The solution was filtered and the filtrate evaporated. The residue in ethyl acetate was washed with sodium bicarbonate solution and dried (Na$_2$SO$_4$). The ethyl acetate solution was diluted with hexane and filtered through silica. The filtrate was evaporated to give the thione (4.5 g, 92%), m.p. 174°-178° C.

EXAMPLE 4

6-Chloro-4,1-benzoxazepin-5-one-2-thione (XI; R$^4$=Cl, R$^5$=H, X=S)

6-Chloro-4,1-benzoxazepin-2,5-dione (10.6 g, 50 mmole) in dimethoxyethane (250 ml) was treated with Lawesson's reagent (12.1 g, 30 mmole) and the mixture stirred at room temperature for 24 hours. The solution was filtered and evaporated. The residue in ethyl acetate was washed with sodium bicarbonate solution and dried (Na$_2$SO$_4$). The solution was diluted with hexane and filtered through silica. The filtrate was evaporated to give the product (11.1 g, 97%), m.p. 177°-180° C.

EXAMPLE 5

5,6-Dihydro-6-oxo-4H-imidazo[1,5-a][4,1]benzoxazepine-3-carbonitrile (VII; R$^4$=R$^5$=H, Y=CN)

4,1-Benzoxazepin-2,5-dione (2.1 g, 12 mmole), N,N-dimethylaniline (13.7 ml) and phosphoryl chloride (1.75 ml, 18 mmole) in dichloromethane (20 ml) was heated under reflux for 18 hours. The solution was cooled and poured into water (50 ml) containing sodium bicarbonate (8 g). The organic layer was separated and the aqueous layer was extracted with dichloromethane. The combined organic phases were washed with water, dried (Na$_2$SO$_4$) and concentrated to give a solution of the imidoyl chloride (VIII; R$^4$=R$^5$=H, W=Cl) in dimethylaniline.

Formamidoacetonitrile (2.2 g, 26 mmole) and triethylamine (8.7 ml) in dichloromethane (26 ml) was treated with phosphoryl chloride (2.5 ml, 25 mmole) at −25° C. and the mixture stirred for 1 hour. The mixture was treated with sodium carbonate (5.3 g) in water (25 ml) at −5° C. and stirred for 45 minutes. The organic layer was separated, washed with water and dried (Na$_2$SO$_4$) to give a solution of isocyanoacetonitrile in dichloromethane.

The isonitrile solution was added to the imidoyl chloride solution containing triethylamine (4.5 ml) and stirred at room temperature for 18 hours. The mixture was poured into 2N HCl (50 ml), the organic layer separated, washed with 2N HCl, saturated sodium bicarbonate and dried (Na$_2$SO$_4$). The solution was evaporated and the residue stirred with hot t-butyl methyl ether. The mixture was cooled and the solid collected, washed with t-butyl methyl ether and dried in vacuo to give the product (1.6 g, 46%), m.p. 220°-221° C.

EXAMPLE 6

7-Chloro-5,6-dihydro-6-oxo-4H-imidazo[1,5-a][4,1]benzoxazepine-3-carbonitrile (VII; R$^4$=Cl, R$^5$=H, Y=CN)

6-Chloro-4,1-benzoxazepin-2,5-dione (25 g, 0.118 mole), phosphoryl chloride (17.5 ml, 0.188 mole) and N,N-dimethylaniline (137 ml, 1.09 mole) in dichloromethane (240 ml) were heated under reflux for 18 hours. The solution was cooled and poured into water (470 ml) containing sodium bicarbonate (82.5 g). The organic layer was washed with water, dried (Na$_2$SO$_4$) and concentrated to give a solution of the imidoyl chloride (VIII; R$^4$=Cl, R$^5$=H, W=Cl) in dimethylaniline.

Formamidoacetonitrile (22.3 g, 0.265 mole) in dichloromethane (263 ml) containing triethylamine (87.2 ml, 0.626 mole) was cooled to −25° C. and phosphoryl chloride (24.8 ml, 0.266 mole) added slowly over ½hour. The mixture was stirred at −20° C. for a further 1 hour and then Na$_2$CO$_3$ (52.6 g) in water (263 ml) was added at below −5° C. The mixture was filtered, the organic layer separated, washed with water and dried to give a solution of isocyanoacetonitrile in dichloromethane.

The solution of the imidoyl chloride in N,N-dimethylaniline was stirred at room temperature with triethylamine (40 ml, 0.288 mole) and the solution of the isocyanoacetonitrile added over 5 minutes. The reaction exothermed from 17.5° C. to 24.5° C. over a period of 2 hours and was stirred overnight at room temperature. The dark reaction mixture was poured into 2N hydrochloric acid (500 ml) and stirred for 5 minutes before separating the organic layer. This was washed with 2N hydrochloric acid (300 ml), saturated sodium bicarbonate solution, dried (Na₂SO₄) and evaporated. The solid was swished with boiling t-butyl methyl ether (75 ml) for 1 hour, and cooled in ice for a further 1 hour. The solid was collected, washed with the minimum of t-butyl methyl ether and dried in air to give the product as a light green crystalline solid (18.3 g, 60%), m.p. 217°–219° C.

EXAMPLE 7

5.6-Dihydro-6-oxo-4H-imidazo[1,5][4,1]benzoxazepine-3-amidoxime 5,6-Dihydro-6-oxo-4H-imidazo[1,5-a][4,1]benzoxazepine-3-carbonitrile (3.8 g, 0.017 mole), potassium carbonate (2.9 g, 0.02 mole), hydroxylamine hydrochloride (1.46 g, 0.02 mole) and water (2.9 ml) were stirred in isopropanol (190 ml) at room temperature for 4 days. The mixture was heated under reflux for 6 hours and then concentrated to 50 ml. The solution was cooled to 5° C. and water (47 ml) added slowly to complete the crystallisation. The solid was collected, washed with water and dried in vacuo at 40° C. to give the product (3.75 g, 86%), m.p. 222°–224° C.

EXAMPLE 8

7-Chloro-5,6-dihydro-6-oxo-4H-imidazo[1,5-a][4,1]benzoxazepine-3-amidoxime

A mixture of 7-chloro-5,6-dihydro-6-oxo-4H-imidazo[1,5-a][4,1]benzoxazepine-3-carbonitrile (16.86 g, 0.06 mole), potassium carbonate (13.5 g, 0.9 mole) and hydroxylamine hydrochloride (4.6 g, 0.06 mole) in isopropanol (843 ml) containing water (13.5 ml) was stirred at room temperature for 4 days. The reaction mixture was then concentrated to a volume of 256 ml by distillation, cooled to room temperature and water (256 ml) added. The resulting mixture was cooled at 0° C. for 1 hour and the solid collected, washed with water and dried in vacuo at 50° C. to give the product (12 g, 63%), m.p. 252°–254° C.

EXAMPLE 9

3-(5-Isopropyl-1,2,4-oxadiazol-3-yl)-5,6-dihydro-6-oxo-4H-imidazo[1,5-a][4,1]benzoxazepine (III)

5,6-Dihydro-6-oxo-4H-imidazo[1,5-a][4,1]benzoxazepine-3-amidoxime (2 g, 8 mmole) in isobutyric anhydride (6 ml) was heated at 150° C. for 1.5 hours. The crude product in ethyl acetate:hexane (1:1) was chromatographed on silica and then crystallised from ethyl acetate:hexane to give the product (1.4 g, 58%), m.p. 143°–144° C.

EXAMPLE 10

3-(5-tert-Butyl-1,2,4-oxadiazol-3-yl)-5,6-dihydro-6-oxo-4H-imidazo[1,5-a][4,1]benzoxazepine (III)

5,6-Dihydro-6-oxo-4H-imidazo[1,5-a][4,1]benzoxazepin-3-amidoxime (I.9 g, 7 mmole) in trimethylacetic anhydride (6 ml) was heated at 150° C. for 1 hour. The crude product in ethyl acetate:hexane (1:1) was chromatographed and then crystallised from ethyl acetate to give the product (1.6 g, 66%), m.p. 210°–211° C.

EXAMPLE 11

7-Chloro-3-(5-methyl-1,2,4-oxadiazol-3-yl)-5,6-dihydro-6-oxo-4H-imidazo[1,5-a][4,1]benzoxazepine (III)

7-Chloro-5,6-dihydro-6-oxo-4H-imidazo[1,5-a][4,1]benzoxazepine-3-amidoxime (3 g, 0.01 mole) in acetic anhydride (9 ml) was heated at 150° C. for 3 hours. The crude product in ethyl acetate was chromatographed on silica and then crystallised from acetone to give the product (2.1 g, 66%), m.p. 253°–255° C.

EXAMPLE 12

7-Chloro-3-(5-propyl-1,2,4-oxadiazol-3-yl)-5,6-dihydro-6-oxo-4H-imidazo[1,5-a][4,1]benzoxazepine (III)

7-Chloro-5,6-dihydro-6-oxo-4H-imidazo[1,5-a][4,1]benzoxazepine-3-amidoxime (2 g, 7 mmole) in n-butyric anhydride (6 ml) was heated at 150° C. for 1 hour. The crude product was chromatographed on silica, initially with ethyl acetate:hexane (1:1) and then changing to ethyl acetate. The purified product was crystallised from ethyl acetate:cyclohexane (4:1) to give the product (1.2 g, 50%), m.p. 130°–132° C.

EXAMPLE 13

7-Chloro-3-(5-pentyl-1,2,4-oxadiazol-3-yl)-5.6-dihydro-6-oxo-4H-imidazo[1,5-a][4,1]benzoxazepine (III)

7-Chloro-5,6-dihydro-6-oxo-4H-imidazo[1,5-a][4,1]benzoxazepine-3-amidoxime (2 g, 7 mmole) in caproic anhydride (8 ml) was heated at 150° C. for 30 minutes. The crude product in ethyl acetate:hexane (1:1) was chromatographed on silica to give the product (1.6 g, 63%), m.p. 110°–112° C.

EXAMPLE 14

7-Chloro-3-(5-isopropyl-1,2,4-oxadiazol-3-yl)-5,6-dihydro-6-oxo-4H-imidazo1,5-a14,1]benzoxazepine (III)

Method A

7-Chloro-5,6-dihydro-6-oxo-4H-imidazo[1,5-a][4,1]benzoxazepine-3-amidoxime (12.6 g, 0.04 mole) in isobutyric anhydride (38 ml) was heated at 150° C. for 1 hour. The crude product in ethyl acetate:hexane (1:1) was chromatographed on silica and crystallised from ethyl acetate to give the product (8.7 g, 60%), m.p. 167°–68° C.

Method B

6-Chloro-4,1-benzoxazepin-2,5-dione (1.9 g, 10 mmole), N,N-dimethylaniline (12.4 ml) and phosphoryl chloride (1.6 ml, 16 mmole) in dichloromethane (20 ml) were heated under reflux for 18 hours. The solution was cooled, poured into water (50 ml) containing sodium bicarbonate (7 g) and the organic phase separated. The aqueous phase was extracted with dichloromethane and the combined phases washed with water, dried (Na₂SO₄) and concentrated to give a solution of the imidoyl chloride. The solution was added to a solution of 3-isocyanomethyl-5-isopropyl-1,2,4-oxadiazole (1.5 g, 10 mmole) in tetrahydrofuran (33 ml). The solution was cooled to −78° C. and treated with lithium diisopropylamide in cyclohexane (1.5 M, 7.4 ml). The solution was stirred at −70° C. for 15 minutes and then at room temperature for 4 hours. The mixture was poured into 2N HCl (50 ml) and the organic layer separated. The aqueous layer was extracted with ethyl acetate and the combined organic layers washed with sodium bicarbonate solution, dried (Na2S04) and evaporated. The crude product in ethyl acetate:hexane (2:1) was chromatographed on silica and crystallised from ethyl acetate to give the product (1.3 g, 43%), m.p. 167°–168° C.

Method C

6-Chloro-4,1-benzoxazepin-5-one-2-thione (6.8 g, 30 mmole) in THF (60 ml) was treated with sodium hydride (0.8 g, 33 mmole) suspended in THF (50 ml) at 10° C. The mixture was aged at 10° C. for 1 hour, treated with methyl iodide (2 ml, 31 mmole) and stirred for a further hour.

The solution of the S-methyl compound was cooled to −78° C., 3-isocyanomethyl-5-isopropyl-1,2,4-oxadiazole (5.6 g, 37 mmole) added followed by lithium diisopropylamide [from butyl-lithium in hexane (2.4 M, 22 ml) and diisopropylamine (7.6 ml) in THF (41 ml)]. The mixture was stirred at < −65° C. for 1.5 hours and then quenched with acetic acid (5 ml). The solution was poured into ethyl acetate (100 ml) and water (100 ml), the organic layer separated and washed with water. The solution was evaporated and the crude product in ethyl acetate:hexane (2:1) chromatographed on silica and crystallised from ethyl acetate to give the product (5.5 g, 53%), m.p. 167°–168° C.

EXAMPLE 15

1-(3-Chloro-2-propylcarboxamidophenyl)-5-hydroxymethyl-4-(5-isopropyl-1,2,4-oxadiazol-3-yl)-imidazole (V)

7-Chloro-3-(5-isopropyl-1,2,4-oxadiazol-3-yl)-5,6-dihydro-6-oxo-4H-imidazo[1,5-a][4,1]benzoxazepine (4 g, 12 mmole) in DMF (20 ml) was treated with excess propylamine and stirred at room temperature for 3 days. The mixture was poured into water and extracted with ethyl acetate. The extract was dried (Na2SO4) and evaporated. The residue was triturated with diethyl ether to give the product (3.5 g, 75%), m.p. 158°–159° C.

EXAMPLE 16

1-(3-Chloro-2-butylcarboxamidophenyl)-5-hydroxymethyl-4-(5-isopropyl-1,2,4-oxadiazol-3-yl)imidazole (V)

7-Chloro-3-(5-isopropyl-1,2,4-oxadiazol-3-yl)-5,6-dihydro-6-oxo-4H-imidazo[1,5-a][4,1]benzoxazepine (3.5 g, 10 mmole) in DMF (20 ml) was treated with excess butylamine and stirred at room temperature for 3 days. The mixture was poured into water and extracted with ethyl acetate. The extract was dried (Na2SO4) and evaporated. The residue was crystallised from ethyl acetate to give the product (2.5 g, 60%), m.p. 127°–128° C.

EXAMPLE 17

1-(3-Chloro-2-methylcarboxamidophenyl)-5-chloromethyl-4-(5-isopropyl-1,2,4-oxadiazol-3-yl)imidazole (VI)

7-Chloro-3-(5-isopropyl-1,2,4-oxadiazol-3-yl)5,6-dihydro-6-oxo-4H-imidazo[1,5-a][4,1]benzoxazepine (5 g, 14.5 mmole) in dimethylformamide (25 ml) was treated with excess methylamine at room temperature for 3 hours. The solution of the hydroxymethyl compound was heated in vacuo at 40° C. to remove methylamine and then cooled to 0° C. Thionyl chloride (1.3 ml, 18 mmole) was added and the solution stirred at 0° C. for 20 minutes. Water (50 ml) was added to the cold solution and the slurry stirred for 2 hours to complete crystallisation. The solid was collected, washed with water and dried in vacuo at 60° C. to give the product (5.3 g, 93%), m.p. 176°–178° C.

EXAMPLE 18

1-(3-Chloro-2-propylcarboxamidophenyl)-5-chloromethyl-4-(5-isopropyl-1,2,4-oxadiazol-3-yl)-imidazole (VI)

1-(3-Chloro-2-propylcarboxamidophenyl)-5-hydroxymethyl-4-(5-isopropyl-1,2,4-oxadiazol-3-yl)imidazole (3 g, 7 mmole) in THF (20 ml) was treated with thionyl chloride (0.6 ml, 8 mmole) and the mixture stirred for 1 hour. The solid was collected, washed with THF and dried in vacuo at 50° C. to give the product (3.1 g, 99%), m.p. 164°–167° C.

EXAMPLE 19

1-(3-Chloro-2-butylcarboxamidophenyl)-5-chloromethyl-4-(5-isopropyl-1,2,4-oxadiazol-3-yl)imidazole (VI)

1-(3-Chloro-2-butylcarboxamidophenyl)-5-hydroxymethyl-4-(5-isopropyl-1,2,4-oxadiazol-3-yl)imidazole (2.4 g, 6 mmole) in THF (20 ml) was treated with thionyl chloride (0.5 ml, 7 mmole) and the mixture stirred for 1 hour. Water (50 ml) was added, the solid collected, washed with water and recrystallised from ethyl acetate to give the product (2.4 g, 95%), m.p. 149°–150° C.

EXAMPLE 20

7-Chloro-3-(5-isopropyl-1,2,4-oxadiazol-3-yl)-5,6-dihydro-5-methyl-6-oxo-4H-imidazo[1,5-a[14,1]benzodiazepine (I)

1-(3-Chloro-2-methylcarboxamidophenyl)-5-chloromethyl-4-(5-isopropyl-1,2,4-oxadiazol-3-yl)imidazole (2 g, 5 mmole) in THF (50 ml) at −30° C. was treated with potassium t-butoxide (0.75 g, 6.25 mmole) in THF (100 ml) and stirred at −30° C. for 15 minutes. Acetic acid (1 ml) was added, the solution diluted with water and the solid collected. The solid was chromatographed on silica with ethyl acetate:hexane (1:1) and then ethyl acetate to give the crude product which was crystallised from ethyl acetate to give the product (1.3 g, 72%), m.p. 165° C. M+·=357.

EXAMPLE 21

7-Chloro-3-(5-isopropyl-1,2,4-oxadiazol-3-yl)-5,6-dihydro-5-propyl-6-oxo-4H-imidazo1,5-a1[4,1]benzodiazepine (I)

1-(3-Chloro-2-propylcarboxamidophenyl)-5-chloromethyl-4-(5-isopropyl-1,2,4-oxadiazol-3-yl)-imidazole (2.1 g, 5 mmole) in THF (100 ml) at −30° C. was treated with potassium t-butoxide (0.6 g, 5 mmole) in THF (55 ml) added over 30 minutes. The solution was poured into water and extracted with ethyl acetate. The extract was concentrated and the solution crystallised. The solid was collected and dried in vacuo at 50° C. to give the product (1.2 g, 60%), m.p. 161°–163° C. M+·=385.

EXAMPLE 22

25

7-Chloro-3-(5-isopropyl-1,2,4-oxadiazol-3-yl)-5,6-dihydro-5-butyl-6-oxo-4H-imidazo1,5-a[4,1]benzodiazepine (I)

1-(3-Chloro-2-butylcarboxamidophenyl)-5-chloromethyl-4-(5-isopropyl-1,2,4-oxadiazol-3-yl)-imidazole (1.75 g, 4 mmole) in THF (87 ml) at −30° C. was treated with potassium t-butoxide (0.5 g, 5 mmole) in THF (50 ml) added over 1 hour. Acetic acid (2 ml) was added, the solution poured into water and extracted with ethyl acetate. The extract was washed with water, dried ($Na_2SO_4$), evaporated and the residue triturated with pentane. The solid was chromatographed on silica with ethyl acetate:hexane (3:2) and the crude product crystallised from ethyl acetate-hexane to give the product (1.0 g, 64%), m.p. 118°–119° C. M+1=400.

EXAMPLE 23

6-Bromo-4,1-benzoxazepin-2,5-dione (XI; $R^4$=Br, $R^5$=H, X=O)

A solution of sodium hydroxide (3.25 g, 81 mmole) in water (20 ml) was added to a stirred slurry of 2-bromo-6-(chloroacetamido)benzoic acid (23 g, 79 mmole) in isopropanol (36 ml) and water (142 ml). The mixture was stirred until a solution formed and then heated at 80° C. for 4 hours. The solution was cooled to 0° C. and the crystalline solid collected, washed with water and dried in vacuo at 50° C. to give the product (18.1 g, 90%), m.p. 210°–212° C.

EXAMPLE 24

7-Bromo-5,6-dihydro-6-oxo-4H-imidazo1,5-a14,1]-benzoxazepine-3-carbonitrile (VII; $R^4$=Br, $R^5$=H, Y=CN)

6-Bromo-4,1-benzoxazepin-2,5-dione (7.23 g, 28 mmole), N,N-dimethylaniline (32.7 ml) and phosphoryl chloride (4.2 ml, 43 mmole) in dichloromethane (48 ml) was heated under reflux for 18 hours. The solution was cooled and poured into water (120 ml) containing sodium bicarbonate (19 g). The organic layer was separated and the aqueous layer was extracted with dichloromethane. The combined organic phases were washed with water, dried ($Na_2SO_4$) and concentrated to give a solution of the imidoyl chloride (VIII; $R^4$=Br, $R^5$=H, W=Cl) in dimethylaniline.

Formamidoacetonitrile (5.23 g, 62 mmole) and triethylamine (21 ml) in dichloromethane (62 ml) was treated with phosphoryl chloride (6 ml, 65 mmole) at −25° C. and the mixture stirred for 1 hour. The mixture was treated with sodium carbonate (12.62 g) in water (60 ml) at −5° C. and stirred for 45 minutes. The organic layer was separated, washed with water and dried ($Na_2SO_4$) to give a solution of isocyanoacetonitrile in dichloromethane.

The isonitrile solution was added to the imidoyl chloride solution containing triethylamine (10.5 ml) and stirred at room temperature for 18 hours. The mixture was poured into 2N HCl (120 ml), the organic layer separated, washed with 2N HCl, saturated sodium bicarbonate and dried ($Na_2SO_4$). The solution was evaporated and the residue stirred with hot t-butyl methyl ether and dried in vacuo to give the product (4.69 g, 55%), m.p. 204°–6° C.

EXAMPLE 25

7-Bromo-5,6-dihydro-6-oxo-4H-imidazo1,5-a1[4,1]-benzoxazepine-3-amidoxime

7-Bromo-5,6-dihydro-6-oxo-4H-imidazo[1,5-a][4,1]benzoxazepine-3-carbonitrile (4 g, 13 mmole), potassium carbonate (2.26 g, 16.4 mmole), hydroxylamine hydrochloride (1.14 g, 16.4 mmole) and water (2.26 ml) were stirred in isopropanol (148 ml) at room temperature for 3 days. The mixture was concentrated to 50 ml. The solution was cooled to 5° C. and water (50 ml) added slowly to complete the crystallisation. The solution was collected, washed with water and dried in vacuo at 40° C. to give the product (3.35 g, 76%), m.p. >240° C.

EXAMPLE 26

5

7-Bromo-3-(5-cyclopropyl-1,2,4-oxadiazol-3-yl)-5,6-dihydro-6-oxo-4H-imidazo[l.5-a1[4,1]benzoxazepine A solution of 7-bromo-5,6-dihydro-6-oxo-4H-imidazo 1,5-a][4,1]benzoxazepine-3-amidoxime (2.43 g, 7.2 mmole) and triethylamine (1.5 ml) in dry tetrahydrofuran (75 ml) was cooled with stirring to 5° C. Cyclopropyl carbonyl chloride (0.83 ml, 1.25 equivs.) was added dropwise under $N_2$ atmosphere and the resulting mixture aged at 5° C. for 5 minutes and then allowed to warm to room temperature. After 30 minutes at room temperature, TLC ($CH_2Cl_2$/MeOH, 95/5) showed the reaction to be complete. The solvent was removed in vacuo to give a solid (2.56 g). Part of this solid (2.47 g) was suspended in xylene (250 ml) containing p-toluenesulphonic acid (0.25 g) and then the mixture was heated to reflux using a Dean and Stark apparatus for 18 hours. The solvent was evaporated and the residue partitioned between water (25 ml) and dichloromethane (25 ml). The aqueous layer was re-extracted with dichloromethane (6×30 ml). The organic extracts were combined, dried ($Na_2SO_4$) and evaporated to give a yellow foam. Trituration with diethyl ether gave the product (1.69 g, 63% overall) as a solid, m.p. 204°–8° C.

EXAMPLE 27

3-(5-Cyclopropyl-1,2.4-oxadiazol-3-vl)-5,6-dihydro-6-oxo-4H-imidazo[1,5-a][4,1]benzoxazepine A solution of 5,6-dihydro-6-oxo-4H-imidazo[1,5-a][4,1]benzoxazepine-3-amidoxime (1.66 g, 6 mmole) and triethylamine (1.36 ml) in dry tetrahydrofuran (50 ml) was cooled with stirring to 5.C. Cyclopropyl carbonyl chloride (0.73 ml, 1.25 equivs.) was added dropwise under $N_2$ atmosphere and the resulting mixture aged at 5° C. for 5 minutes and then allowed to warm to room temperature, when TLC ($CH_2Cl_2$/MeOH, 95/5) showed the reaction to be complete. The solvent was removed in vacuo to give a yellow solid (1.75 g). The solid was suspended in xylene (250 ml) containing p-toluenesulphonic acid (0.18 g) and then the mixture was heated to reflux using a Dean and Stark apparatus for 20 hours. The solvent was evaporated and the residue partitioned between water (25 ml) and dichloromethane (25 ml). The aqueous was re-extracted with dichloromethane (6×30 ml). The organic extracts were combined, dried ($Na_2SO_4$) and evaporated to give a yellow foam. Trituration with diethyl ether gave the product (1.26 g, 76%) as a beige solid, m.p. 206°–209° C.

EXAMPLE 28

1-(3-Bromo-2-methylcarboxamidophenyl)-5-chloromethyl-4-(5-cyclopropyl-1,2,4-oxadiazol-3-yl)-imidazole 7-Bromo-3-(5-cyclopropyl-1,2,4-oxadiazol-3-yl)-5,6-dihydro-6-oxo-4H-imidazo[1,5-a][4,1]benzoxazepine (1.5 g, 4 mmole) in DMF (30 ml) was treated with excess gaseous methylamine at room temperature and stirred overnight. The excess methylamine was removed at 40° C. in vacuo and the solution cooled to 0° C. Thionyl chloride (0.75 ml) was added and the solution stirred at room temperature for 30 minutes. Water (60 ml) was added, the mixture stirred at 0°-5° C. for 2 hours and then filtered. The solid was washed with water (10 ml) and dried in vacuo at 50° C., to give the product (1.21 g, 72%) as a solid, m.p. 177°-180° C.

EXAMPLE 29

1-(2-Methylcarboxamidophenyl)-5-chloromethyl-4-(5-cyclopropyl-1,2,4-oxadiazol-3-yl)-imidazole 3-(5-Cyclopropyl-1,2,4-oxadiazol-3-yl)-5,6-dihydro-6-oxo-4H-imidazo[1,5-a][4,1]benzoxazepine (1.08 g, 3.5 mmole) in DMF (45 ml) was treated with excess gaseous methylamine at room temperature and stirred overnight. The excess methylamine was removed at 40° C. in vacuo and the solution cooled to 0° C. Thionyl chloride (0.5 ml) was added and the solution stirred at room temperature for 30 minutes. Water (65 ml) was added, the mixture stirred at 0°-5° C. for 2 hours and then filtered. The solid was washed with water (10 ml) and dried in vacuo at 50° C., to give the product (0.87 g, 69%) as a solid, m.p. 188°-189° C.

EXAMPLE 30

7-Bromo-3-(5-cyclopropyl-1,2,4-oxadiazol-3-yl)-5,6-dihydro-5-methyl-6-oxo-4H-imidazo[1,5-a][1,4]benzodiazepine (I)

1-(3-Bromo-2-methylcarboxamidophenyl)-5-chloromethyl-4-(5-cyclopropyl-1,2,4-oxadiazol-3-yl)imidazole (0.88 g, 2 mmole) in THF (25 ml) at −30° C. was treated with potassium t-butoxide (0.3 g, 2.6 mmole) in THF (25 ml) added over 1 hour. Acetic acid (0.5 ml) was added, and the solvent removed in vacuo. Water (25 ml) was added to the residual oil which solidified when cooled in ice. The resulting mixture was aged in ice for 2 hours, filtered, washed with water (10 ml) and dried in vacuo at 50° C. overnight to give the crude product (0.813 g, 100%). The solid was chromatographed on silica with ethyl acetate to give product (0.74 g, 92%) as a yellow solid which was recrystallised from isopropanol/methanol (3/2) to give the pure product (0.52 g) as an off-white solid, m.p. 213°-215° C. M+· = 399:401 (1:1).

EXAMPLE 31

3-(5-Cyclopropyl-1,2,4-oxadiazol-3-yl)-5,6-dihydro-5-methyl-6-oxo-4H-imidazo1,5-a][1,4]benzodiazepine (I)

1-(2-Methylcarboxamidophenyl)-5-chloromethyl-4-(5-cyclopropyl-1,2,4-oxadiazol-3-yl)imidazole (0.64 g, 1.8 mmole) in THF (25 ml) at −30° C. was treated with potassium t-butoxide (0.3 g, 2.6 mmole) in THF (25 ml) added over 1 hour. Acetic acid (0.5 ml) was added, and the solvent removed in vacuo. Water (25 ml) was added to the residual oil which solidified when cooled in ice. The resulting mixture was aged in ice for 2 hours, filtered, washed with water (10 ml) and dried in vacuo at 50° C. overnight to give the crude product (0.5 g, 86%) which was recrystallised from isopropanol/methanol (3/2) to give the pure product (0.3 g) as an off-white solid, m.p. 189°—190° C. M+· = 321.

What is claimed is:

1. A compound of Formula [III]:

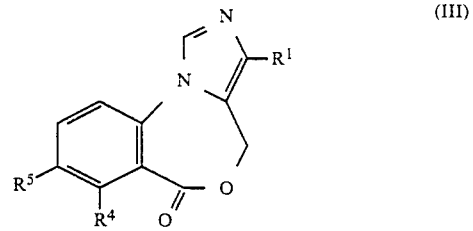

(III)

wherein $R^1$ is an aromatic heterocyclic group containing 5 or 6 atoms, up to 3 of which are selected from the group consisting of oxygen, nitrogen and sulfur, any of which groups may be unsubstituted or substituted on a carbon atom by a substituent selected from the group consisting of $C_{1-5}$ alkyl, $C_{3-6}$ cycloalkyl, trifluoromethyl, phenyl, amino, $C_{1-6}$ alkylamino, $C_{1-6}$ alkoxy ($C_{1-6}$) alkyl and hydroxy and $R^4$ and $R^5$ are independently selected from the group consisting of hydrogen, halogen, trifluoromethyl, cyano, nitro, amino and lower alkyl.

2. The compound according to claim 1, wherein $R^4$ and $R^5$ are independently selected rom the group consisting of hydrogen, halogen and trifluoromethyl.

3. The compound according to claim 1, wherein $R^1$ is selected from the group consisting of 1,2,4-oxadiazol-3-yl; 1,2,4-oxadiazol-5-yl; 1,3,4-oxadiazol-2-yl; 1,2,4-thiadiazol-3-yl; 1,3,4-thiadiazol-2-yl and 1,2,5-thiadiazol-3-yl.

4. The compound according to claim 2, wherein $R^1$ is selected from the group consisting of 1,2,4-oxadiazol-3-yl; 1,2,4-oxadiazol-5-yl; 1,3,4-oxadiazol-2-yl; 1,2,4-thiadiazol-3-yl; 1,3,4-thiadiazol-2-yl and 1,2,5-thiadiazol-3-yl.

5. The compound according to claim 1, represented by formula IV:

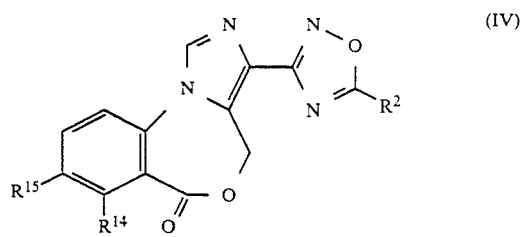

(IV)

wherein $R^{14}$ and $R^{15}$ are independently selected from the group consisting of hydrogen, fluoro, chloro and bromo; and $R^2$ is selected from the group consisting of hydrogen, $C_{1-4}$ alkyl and $C_{3-6}$ cycloalkyl.

6. The compound according to claim 5, wherein $R^2$ is selected from the group consisting of hydrogen, methyl, n-propyl, isopropyl, t-butyl and cyclopropyl.

7. The compound according to claim 3, wherein any of the $R^1$ groups may be unsubstituted or substituted on a carbon atom by an alkyl or cycloalkyl substituent.

8. The compound according to claim 2, wherein any of the $R^1$ groups may be unsubstituted or substituted on a carbon atom by an alkyl or cycloalkyl substituent.

* * * * *